US009878452B2

(12) United States Patent
Davis et al.

(10) Patent No.: US 9,878,452 B2
(45) Date of Patent: Jan. 30, 2018

(54) GRASP ASSIST DEVICE WITH AUTOMATIC MODE CONTROL LOGIC

(71) Applicants: GM GLOBAL TECHNOLOGY OPERATIONS LLC, Detroit, MI (US); The United States of America As Represented by the Administrator of the National Aeronautics and Space Administration, Washington, DC (US)

(72) Inventors: Donald R. Davis, Novi, MI (US); Chris A. Ihrke, Hartland, MI (US); Evan Laske, Webster, TX (US)

(73) Assignees: GM Global Technology Operations LLC, Detroit, MI (US); The United States of America As Represented by the Administrator of the National Aeronautics and Space Administration, Washington, DC (US)

( * ) Notice: Subject to any disclaimer, the term of this patent is extended or adjusted under 35 U.S.C. 154(b) by 174 days.

(21) Appl. No.: 14/739,428

(22) Filed: Jun. 15, 2015

(65) Prior Publication Data

US 2016/0361820 A1 Dec. 15, 2016

(51) Int. Cl.
| | |
|---|---|
| *B25J 13/08* | (2006.01) |
| *A61B 5/00* | (2006.01) |
| *A61F 2/68* | (2006.01) |
| *G01S 19/19* | (2010.01) |
| *G06F 3/01* | (2006.01) |
| *A41D 19/00* | (2006.01) |

(52) U.S. Cl.
CPC .............. *B25J 13/08* (2013.01); *A61B 5/6804* (2013.01); *A61F 2/68* (2013.01); *G01S 19/19* (2013.01); *G06F 3/014* (2013.01); *A41D 19/0024* (2013.01); *Y10S 901/36* (2013.01)

(58) Field of Classification Search
CPC ..................................................... Y10S 901/36
See application file for complete search history.

(56) References Cited

U.S. PATENT DOCUMENTS

| | | | | |
|---|---|---|---|---|
| 8,255,079 | B2 * | 8/2012 | Linn ...................... | B25J 9/0006 482/47 |
| 8,849,453 | B2 * | 9/2014 | Bergelin ................ | B25J 9/0006 600/595 |
| 9,067,325 | B2 * | 6/2015 | Ihrke ........................ | B25J 15/02 |
| 9,104,271 | B1 * | 8/2015 | Adams .................. | G06F 3/0426 |
| 9,120,220 | B2 * | 9/2015 | Bergelin ................ | B25J 9/0006 |

(Continued)

*Primary Examiner* — Nicholas Kiswanto
(74) *Attorney, Agent, or Firm* — Quinn IP Law

(57) ABSTRACT

A system includes a glove, sensors, actuator assemblies, and controller. The sensors include load sensors which measure an actual grasping force and attitude sensors which determine a glove attitude. The actuator assembly provides a grasp assist force to the glove. Respective locations of work cells in the work environment and permitted work tasks for each work cell are programmed into the controller. The controller detects the glove location and attitude. A work task is selected by the controller for the location. The controller calculates a required grasp assist force using measured actual grasping forces from the load sensors. The required grasp assist force is applied via the glove using the actuator assembly to thereby assist the operator in performing the identified work task.

18 Claims, 2 Drawing Sheets

(56) References Cited

U.S. PATENT DOCUMENTS

2010/0156783 A1* 6/2010 Bajramovic ............ G06F 1/163
                                                         345/156
2013/0219586 A1    8/2013 Ihrke et al.
2013/0226350 A1    8/2013 Bergelin et al.

* cited by examiner

GRASP ASSIST DEVICE WITH AUTOMATIC MODE CONTROL LOGIC

STATEMENT REGARDING FEDERALLY SPONSORED RESEARCH OR DEVELOPMENT

This invention was made with government support under NASA Space Act Agreement number SAA-AT-07-003. The invention described herein may be manufactured and used by or for the U.S. Government for U.S. Government (i.e., non-commercial) purposes without the payment of royalties thereon or therefor.

TECHNICAL FIELD

The present disclosure relates to a grasp assist device with automatic mode control logic.

BACKGROUND

Ergonomics is an evolving scientific discipline that ultimately seeks to understand and improve human interactions with the various pieces of equipment used within a work environment, such as keyboards, workstations, torque wrenches, control input devices, and the like. Modern ergonomic design practices seek to optimize all aspects of an operator's physical work environment. Even so, repetitive motion may adversely affect product quality and process efficiency over time.

For some types of repetitive tasks requiring application of a grasping force by an operator to a tool or other object, the operator's grip strength may gradually decline over the course of a work day. Grip strength can also vary widely between different operators performing the same work tasks, e.g., due to differences in strength, physical stature, or muscle fatigue. The variable nature of a given operator's grip strength may result in relatively inefficient execution of certain grasp-related work tasks in a work environment.

SUMMARY

A system and an associated control method are disclosed herein for a grasp assist device, such as a glove-based grasp assist device of the type generally known in the art. The range of possible work tasks for a given work environment may vary from relatively coarse actions such as heavy lifting and positioning of a relatively large object, for instance a vehicle wheel, to finer actions such as positioning and installing fasteners. As such, existing control schemes for conventional grasp assist devices, which typically require manual determination and selection of an appropriate control mode by an operator using a user interface, may be less than optimal when used in certain types of work environments. The present design is therefore intended to address some of these performance concerns by offloading the grasp assist mode selection decision process and implementation from the operator to an onboard controller.

The grasp assist device disclosed herein adds a sensor array and associated control logic to help improve the performance of prior art grasp assist devices. The sensor array enables the controller to automatically locate the grasp assist device within a work environment and determine a location of an operator wearing the grasp assist device. The sensors in the array also detect an attitude of the grasp assist device, for example pitch, roll, yaw, acceleration, magnetic field, and/or general orientation of various portions of the device. Collectively, the location and attitude data allow the controller, with minimal required input from the operator, to automatically select an appropriate grasp control mode that is suitable for the work task at hand. Optional features may be programmed into the controller such as a calibration mode and an on/off gesture detection mode as set forth herein to further optimize performance of the grasp assist device.

The operator may wear a glove portion of the present grasp assist device on a hand. In such an embodiment, multiple flexible tendons are selectively tensioned with a calculated tensile force by a corresponding actuator assembly, for example a motorized ball screw. The actuator assembly applies tension to one or more of the tendons to help close the operator's hand into a predetermined grasp pose. Load sensors positioned on the finger and thumb portions or other surfaces of the glove collectively provide force feedback signals to the controller. The controller then calculates and commands a required tensile force from the various tendons at levels that depend on the particular work task being performed by the operator. All of this occurs in conjunction with the location- and attitude-based automatic control mode selection described herein.

In general, as an operator moves through a facility wearing the grasp assist device, the controller automatically identifies the operator's location/heading and a target work cell, either via measurement/detection or calculation, and thereafter automatically restricts operation of the grasp assist device to a subset of permitted work tasks, for instance by automatically selecting from a global list of predetermined work tasks programmed into the controller's memory. GPS or RFID sensors are possible example location sensors usable as part of the sensor array, when location is detected, to provide the required location/heading data to the controller. Within the work cell itself, the attitude sensors collectively determine the attitude of the glove or other portion of the grasp assist device, e.g., using joint angle sensors and/or accelerometers positioned on various surfaces of the grasp assist device. Thereafter, the controller closely restricts permitted functions of the grasp assist device to a particular work task or tasks selected by the controller from the restricted list of predetermined work tasks.

The location and/or the attitude of the grasp assist device can also be used to turn the grasp assist functionality on or off as needed, such as when the operator steps out of the work cell into an adjacent walkway, a break area, or another designated area in which operation of the grasp assist device is not desirable, and/or when the operator moves the grasp assist device with a predetermined gesture signaling a desire to temporarily discontinue or disable grasp assist functionality regardless of location.

In some embodiments, a mobile or static data display device in communication with the controller can receive and display information in a manner that is dependent upon where the operator is in the facility. For example, the display device may present a build schedule or other build information, work steps, production cues, and the like.

In particular, a system as set forth herein includes a glove, an array of sensors, an actuator assembly, and a controller. The sensors are positioned with respect to the glove, and include load sensors which measure an actual grasping force applied to an object by the operator while wearing the glove, and attitude sensors which collectively determine an attitude of the glove, and which may be used to determine the location alone and/or with optional location sensors. The actuator assembly or assemblies are operable for providing a grasp assist force to the glove.

The controller is programmed with a set of coordinates for work cells in the work environment, and also with a set of permitted work tasks for each of the work cells. The controller is further programmed to detect a location of the operator within the work environment and an attitude of the glove within the detected location. Additionally, the controller selects a work task from a list of permitted work tasks for the detected location using the determined location and attitude, and receives a measured actual grasping force via the load sensors. The controller then calculates a grasp assist force suitable for assisting in performing of the identified work task using the measured grasping force and automatically selects and applies the required grasp assist force to the glove via the actuator assembly. In this manner, the operator is assisted in performing the identified work task.

An associated method is also disclosed. In a possible embodiment the method includes the steps of determining the location of the operator and then determining the attitude of the glove within the determined location using the attitude signals. The method also includes identifying a work task from a list of permitted work tasks for the determined location using the determined location and attitude, measuring an actual grasping force applied by the operator to an object via the load sensors, and calculating the required grasp assist force for the identified work task using the measured actual grasping force. Thereafter, the method includes commanding application of the required grasp assist force to the glove via the actuator assembly using the controller to thereby assist the operator in performing the identified work task.

The above-described and other features and advantages of the present disclosure are readily apparent from the following detailed description of the best modes for carrying out the disclosure when taken in connection with the accompanying drawings.

DETAILED DESCRIPTION

Figure 1:
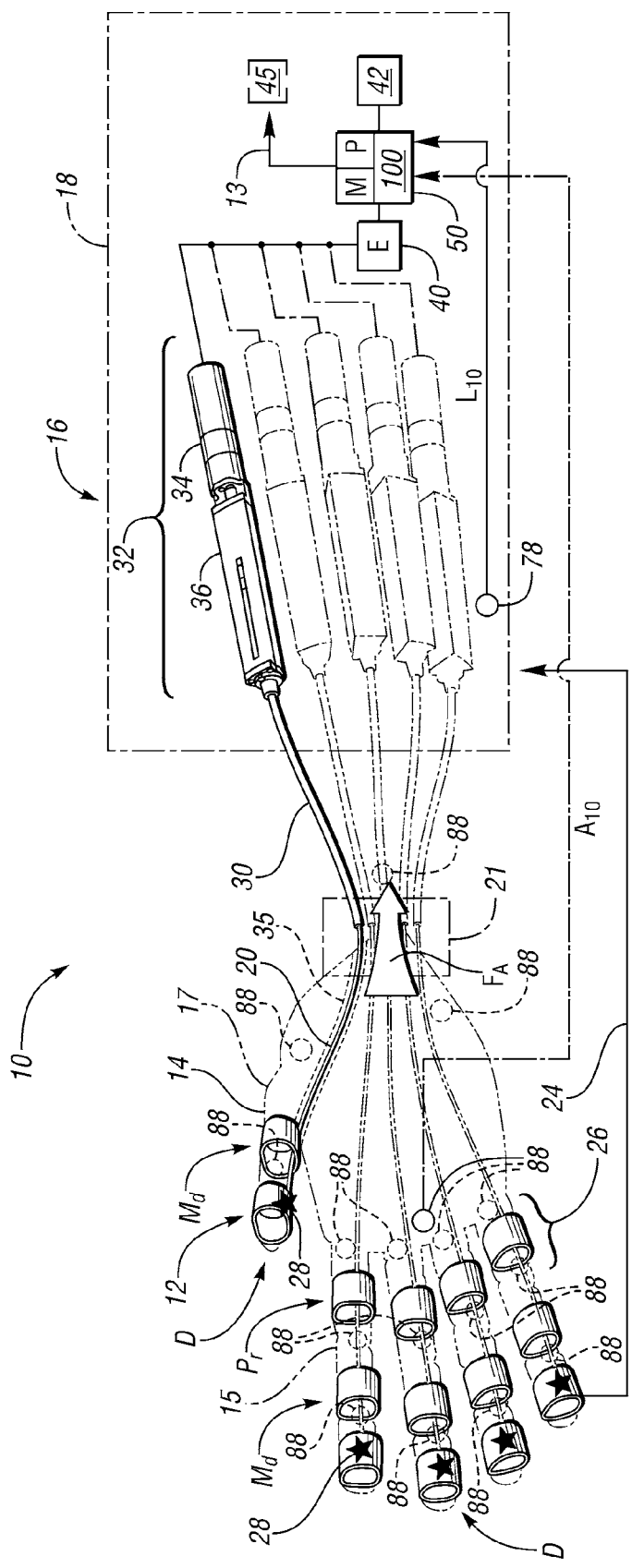
FIG. 1 is a schematic illustration of an example grasp assist device and an associated controller configured to automatically control mode selection of the grasp assist device as set forth herein.

With reference to the drawings, wherein like reference numbers refer to the same or similar components throughout the several views, an example grasp assist device 10 is shown in FIG. 1 having a controller 50. The grasp assist device 10 may include a glove 12 and a sleeve 18. When the grasp assist device 10 is worn on a hand and forearm of an operator, the device automatically assists the operator in grasping an object and/or performing any number of manual work tasks. The range of possible work tasks in a given work environment may vary from relatively coarse actions such as heavy lifting or general positioning of relatively large objects such as vehicle wheels to fine motor skills such as locating and installing fasteners or supporting body panels during an installation process.

Existing control schemes used for conventional grasp assist devices may be less than optimal in facilities having a large variety of work tasks divided into different work cells, as such designs tend to require a mode decision and affirmative selection by an operator. For example, an operator may be required to alert a controller as to the particular task to be performed, or select a desired grasp assist level, or the grasp assist device may be programmed to provide only a limited range of predetermined grasp assist levels. The present design is intended to address this control problem by offloading the control decision to the controller in cooperation with a sensor array as described herein, and to thereby optimize operator efficiency when performing device-assisted work tasks.

Apart from the automatic control functionality described below with reference to FIGS. 2-4, which utilizes control signals from a location sensor 78 and a plurality of attitude sensors 88 shown at example locations in FIG. 1, or derives location from the attitude sensors 88 while forgoing use of the location sensor 78 in another embodiment, the controller 50 also calculates and applies an assisting tensile force (arrow $F_A$) to one or more flexible tendons 20, as is well known in the art. A tendon drive system (TDS) 16 contained fully or partially within the sleeve 18 and linked to the glove 12 via the tendon(s) 20 may be used for such a purpose, with the assisting tensile force (arrow $F_A$) applied to some or all of the flexible tendons 20 in response to force feedback signals (arrow 24) received by the controller 50 from one or more load sensors 28 positioned with respect to the glove 12. Such load sensors 28 are indicated in FIG. 1 as stars for illustrative clarity. The locations and/or numbers of the load sensors 28 may vary from those shown in FIG. 1 and therefore are not limited to fingertip placement as shown.

The glove 12 may include one or more digit portions, i.e., a thumb portion 14 and/or one or more finger portions 15. The glove 12 may be configured as a conventional full four-finger/one thumb glove as shown, or with fewer fingers 15/no thumb 14 in other embodiments. Connected to material 17 of the glove 12, for example sewn in place, may be a plurality of phalange rings 26 or another suitable load bearing structure. Each of the phalange rings 26 may at least partially circumscribe a digit of the operator's hand, i.e., by at least partially circumscribing a respective one of the thumb portion 14 or finger portions 15 of the glove 12. Alternatively, the phalange rings 26 may be positioned within the thumb portion 12/finger portions 15. Thus, any tensile force (arrow $F_A$) imparted by some or all of the tendons 20 can indirectly act on an operator's actual fingers/thumb through the phalange rings 26.

The load sensors 28 shown in FIG. 1 may be positioned with respect to the glove 12 such as at a medial (arrow Md) portion or distal end (arrow D) of the thumb portion 14 and/or the finger portions 15, or alternatively on a palm of the glove 12. Only one load sensor 28 may be used in an alternative embodiment. The location sensor 78 and the attitude sensor(s) 88 may be disposed on one or more of the thumb portion 14 and/or the finger portions 15, or the palm, with the load sensors 28, the location sensor 78, and the attitude sensor(s) 88 collectively forming a sensor array of the grasp assist device 10.

Within the sensor array, the load sensors 28 are used to signal a desired grasp/grasp release, and to trigger a corresponding controlled application or discontinuation of the tensile force (arrow $F_A$) as noted above. The location sensor 78 is used to detect a present location and also calculate a direction or heading of the grasp assist device 10 in a work cell as needed, as set forth below with reference to FIG. 2, and to further restrict the range of allowable control modes for a given work cell. The attitude sensor(s) 88 in turn are used by the controller 50 to select from the restricted list of allowed work tasks for the operator's present work cell, and to possibly execute other control modes including a calibration mode and an on/off mode as described below with reference to FIG. 3.

Examples of the attitude sensors 88 include any wireless location positioning sensors, transceivers, receivers, or devices operable to determine an orientation or pose of the grasp assist device 10 within an inertial frame of reference, and/or for determining the location of the glove 12 when a dedicated location sensor 78 is not used, for instance joint angle sensors, gyroscopes, digital compasses, accelerometers, altimeters, magnetometers, and the like. Such devices may include multi-axis motion tracking chip-based devices of the types known in the art for use in smartphones and wearable sensors. For instance, magnetometers may be used to determine orientation of the glove 12 with respect to earth's magnetic field, as is known in the art, and when used in conjunction with accelerometers can help eliminate drift from any derived location when locations sensors 78 are not used. More or fewer attitude sensors 88 may be used in a given design relative to the number shown in FIG. 1. Likewise, the locations of the attitude sensors 88 may vary. In an example configuration, a respective joint angle sensor may be positioned at the wrist and finger/thumb portions of the glove 12, and one or more accelerometers may be positioned on the glove 12.

With respect to the optional location sensor(s) 78, a radio frequency identification (RFID) sensor system may be used in one possible approach. As is well known in the art, typical RFID sensors suitable for indoor use include wireless RFID tags and antennas. When used with the grasp assist device 10 of FIG. 1, the attitude sensors 88 may be embodied as such RFID tags, with the required location information transmitted to or from the RFID tags by way of fixed antennas, e.g., one per work cell, to thereby alert the controller 50 to the present position of the device 10. When configured as an alternative global positioning system (GPS) device, the location sensor 78 may be embodied as a GPS receiver communicating with a navigation satellite (not shown) so as to determine the geospatial coordinates of an operator wearing the grasp assist device 10. The use of GPS receivers in an indoor facility, however, may be less than optimal due to the presence of a roof and walls, which can interfere with GPS signals. As noted above, the function of the location sensor 78 may be provided by some or all of the attitude sensors 88, e.g., by deriving the location of the glove 12 from the attitude sensors 88 as based on changes in the values of the attitude signals (arrow $A_{10}$).

In general, a grasp force exerted on an object in the operator's grasp activates the load sensor(s) 28. The phalange rings 26 in turn are connected to the tendons 20 that run through the phalange rings 26, with at least some of the phalange rings 26 acting as guides for the tendons 20. Two types of phalange rings 26 may be provided herein: the phalange rings positioned at the distal end (arrow D) of each finger portion 15 and thumb portion 14, and respective medial (arrow Md) and proximal (arrow Pr) phalange rings 26. In some embodiments, the tendons 20 may terminate at the distal (arrow D) phalange rings 26, while the medial (arrow Md) and proximal (arrow Pr) phalange rings 26 are primarily used to guide or direct the tendons 20 and to support the operator's finger. However, other configurations may be envisioned within the intended inventive scope.

The load sensors 28 may be positioned and configured to sense only the grasping force applied by the operator to an object. In this embodiment, the load sensor(s) 28 may be positioned on an inner surface of the distal phalange rings 26 (arrow D). Other designs may also be used without departing from the intended scope of the control method 100 shown in FIG. 4 and described below.

When an object is grasped by an operator, the actual grasping force or pressure applied by the operator to an object is measured by the load sensor(s) 28 and relayed as the force feedback signals (arrow 24) to the controller 50, which may be worn on/in the sleeve 18 of the grasp assist device 10 or located external to the device 10 and controlled wirelessly. Each of the load sensors 28 may be configured as a pressure transducer or any other suitable load or contact cell that precisely measures the amount of force between the load sensor 28 and any object grasped by the operator. Additionally, a location signal (arrow $L_{10}$) and an attitude signal ($A_{10}$) are received and processed by the controller 50 from the respective location sensor 78 and attitude sensor(s) 88.

With respect to the tendons 20, each of the tendons 20 may be optionally configured as a braided polymer, e.g., fluorocarbon, to increase the wear life of each tendon 20. However, other materials and/or designs may also be used without departing from the intended scope of the invention. The tendons 20 may pass through an optional tendon concentrator 21 located on or near the base of the palm or wrist area of the operator. The tendons 20 run through the conduit 30 for at least part of the lengths of the tendons 20, and freely between the tendon concentrator 21 and the phalange rings 26. This arrangement may help isolate the grasping assist motion to the area on the operator's hand from the fingertips to the base of the operator's palm, i.e., isolate the effect of any augmenting tensile force to the area between the tendon concentrator 21 and the phalange rings 26. From the finger side of the tendon concentrator 21 to the distal phalange rings 26, the tendons 20 may be contained in channels 35 embedded or contained within the material of the glove 12.

As shown in phantom, multiple actuator assemblies 32, for instance motorized ball screw devices, may be configured in an array within the TDS 16. Each actuator assembly 32 acts on a portion of a corresponding flexible tendon 20. While not shown for illustrative simplicity, a tendon 20 may loop through a nut within a given one of the actuator assemblies 32 so that the tendon 20 can slide freely, with ends of the tendons 20 attached, for example, to different finger portions 15. In such a design, as one finger portion 15 grasps or comes in contact with an object, the tendon 20 will slide through the nut so the other finger portion 15 can continue to grasp or close. Thereafter, the actuator assembly 32 can apply a grasping force to both finger portions 15. Other tendon-driven designs may be envisioned, as well as drive systems that do not use tendons, without departing from the intended scope. When only one TDS 16 is used, the tendon concentrator 21 may be used to connect the flexible tendons 20 leading from a thumb portion 14 and each finger portion 15 to a single actuator tendon, i.e., the flexible tendon shown via solid lines in FIG. 1. In this case, the tendon concentrator 21 provides an area for the multiple flexible tendons 20 to be connected to a single tendon.

Still referring to FIG. 1, the actuator assembly 32 may include a servo motor 34 and a drive assembly 36, e.g., a ball screw-type linear actuator device according to one possible embodiment. Operation of the TDS 16 is provided via the controller 50, which draws any required power from an energy supply (E) 40. The energy supply 40 may be configured as a miniature battery pack, e.g., a lithium ion cell or cells, or any other relatively lightweight or low-mass energy storage device. An optional sleeve display 42 may be connected to the sleeve 18 and placed in communication with the controller 50 to display a controller-selected selected control mode. The sleeve display 42 may be a small operator-accessible control panel, touchpad, or touch screen allowing an operator to view a particular mode of operation or other message.

The controller 50 may include one or more integrated circuits, which may be augmented by various electronic devices such as voltage regulators, capacitors, drivers, timing crystals, communication ports, etc. The controller 50 may be a microcontroller having a processor and memory, e.g., optical or magnetic read only memory (ROM), as well as sufficient amounts of random access memory (RAM) and/or electrically-programmable read only memory (EPROM), input/output (I/O) circuitry, signal conditioning and buffer electronics, and the like. Output signals (arrow 13) may be transmitted to an optional static or mobile display screen 45 (see FIG. 2) to communicate detailed task-related information to the operator in the performance of a given work task.

Figure 2:
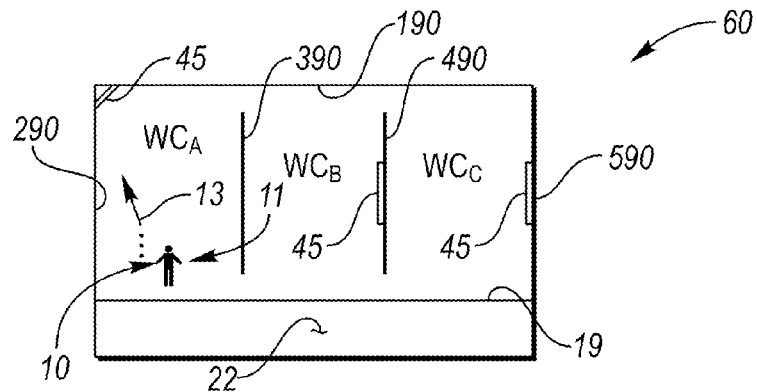
FIG. 2 is a schematic illustration of an operator wearing the grasp assist device of FIG. 1 while moving within an example work environment having multiple designated work task areas.

Referring to FIG. 2, an example work environment 60 is shown schematically as having three different work cells $WC_A$, $WC_B$, and $WC_C$ defined by boundaries 19, 190, 290, and 590. As is typical of manufacturing facility layouts, the work cells $WC_A$, $WC_B$, and $WC_C$ may be located adjacent to a walkway 21, i.e., a demarcated corridor a walkway along which an operator 11 can freely move. The work cell $WC_A$ may be separated from the work cell $WC_B$ by an inner boundary 390. Similarly, work cell $WC_B$ may be separated from work cell $WC_C$ by an inner boundary 490.

The boundaries 19, 190, 290, 390, 490, and 590 may be real or imaginary. For example, while walls or other solid physical barriers may be used to separate the work cells $WC_A$, $WC_B$, and $WC_A$ from each other and/or from the walkway 21, the boundaries 19, 190, 290, 390, 490, and 590 may simply denote defined imaginary perimeters of the work cells $WC_A$, $WC_B$, and $WC_A$. In either case, the coordinates of each of the boundaries 19, 190, 290, 390, 490, and 590 may be programmed into memory M of the controller 50 of FIG. 1 and thus are known by the controller 50.

As the operator 11 wearing the grasp assist device 10 moves within the work environment 60 of FIG. 2, the controller 50 is continuously updated as to the location and heading of the operator 11 primarily via operation of the location sensor 78 of FIG. 1. Therefore, while the operator 11 is traveling along the walkway 21 or is otherwise not present in any of the work cells $WC_A$, $WC_B$, or $WC_C$, the controller 50 may maintain the grasp assist device 10 in an off or standby state. In such an embodiment, the grasp assist device 10 automatically powers down when the operator 11 departs a work cell $WC_A$, $WC_B$, or $WC_C$ and does not enter another adjacent work cell. While in a work cell $WC_A$, $WC_B$, or $WC_C$, the operator 11 may optionally request deactivation of the grasp assist device 10 via a predetermined gesture as noted below with reference to FIG. 3.

To enable the functionality noted above, the controller 50 may be programmed with the geographic coordinates of the various work cells in the work environment 60. Thus, the controller 50 may compare received location signals from the location sensor 78 of FIG. 1 to predetermined coordinates demarcating the boundary lines 190, 290 noted above. In this manner, the controller 50 is able to determine the physical location and heading of the operator 11 relative to the work environment 60. Control of the device 10 proceeds in a different manner once the operator 11 arrives at a given work cell.

With respect to the optional display screens 45, such devices may be static display screens such as video monitors in wireless communication with the controller 50 of FIG. 1. Because the size of the sleeve 18 is limited, a comparatively large screen 45 may be arranged in each work cell $WC_A$, $WC_B$, and $WC_C$, or may be worn by the operator 11, e.g., as a smart phone or glasses, such that the operator 11 is alerted via test, sound, video, and the like as to information pertaining to the task at hand. For example, as the controller 50 selects a predetermined task for a given work cell $WC_A$, $WC_B$, or $WC_C$, the display screen 45 for the particular work cell can present information such as a build schedule, sequence, or instructions in response to receipt of the output signal (arrow 13) from the controller 50.

Figure 3:
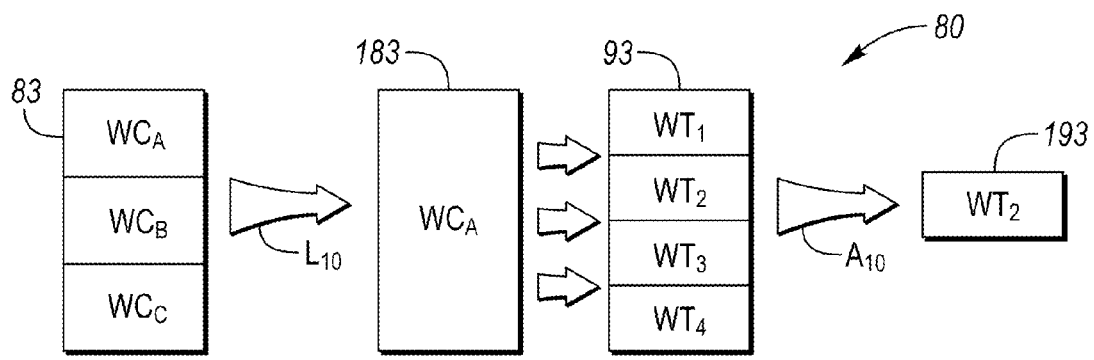
FIG. 3 is a schematic logic flow diagram describing the programmed mode selection operation of the controller of FIG. 1.

Referring to FIG. 3, a logic flow diagram 80 depicts the location and attitude sensing functionality of the controller 50 of FIG. 1. A representative table 83 of possible work cells $WC_A$, $WC_B$, and $WC_C$ is programmed into memory (M) of the controller 50 shown in FIG. 1, with the three work cells $WC_A$, $WC_B$, and $WC_C$ shown for consistency with the non-limiting embodiment of FIG. 2. For a given grasp assist device 10, the table 83 may include all possible work cells in a given work environment 60 or just a subset of such work cells, such that the grasp assist device 10 will only work in certain areas. Location signals (arrow $L_{10}$) from the optional location sensor 78 as shown in FIG. 1 may be transmitted to the controller 50 in some embodiments, and as the operator 11 enters a given work cell, e.g., work cell $WC_A$, a corresponding work cell table 183 is accessed by the controller 50, with the work cell table 183 including a calibrated list of work tasks 93 authorized for that specific work cell. When the location sensor 78 is not used, location may be derived via the attitude sensors 88 as noted above.

The calibrated list of work tasks 93 includes example work tasks $WT_1$, $WT_2$, $WT_3$, and $WT_4$ as shown. For instance, for a given work cell $WC_A$ the operator 11 of FIG. 2 may be permitted to grasp and lift a vehicle wheel as work task $WT_1$, place the wheel onto a hub of a vehicle as the work task $WT_2$, secure the positioned wheel via placement of nuts as work task $WT_3$, and fasten the nuts via a torque wrench as the work task $WT_4$. Each work task may correspond to a different set of grasp assist parameters, e.g., different tensile forces ($F_A$) acting on different finger portions 15 and/or the thumb 14, which in turn may vary with each operator 11 wearing the grasp assist device 10. For instance, for example work task $WT_1$, a maximum amount of assisting force may be provided at all finger portions 15 and the thumb portion 14, while only the thumb portion 14 and one finger portion 15 may be activated for work tasks $WT_3$ and $WT_4$.

In order to quickly differentiate between all of the possible work tasks in the example work cell $WC_A$, the controller 50 receives and processes signals (arrow $A_{10}$) from the attitude sensor(s) 88 of FIG. 1. Example signals include acceleration of a palm of the grasp assist device 10, and/or pitch, yaw, and roll of different portions of the glove 12. In other words, the controller 50 detects a gesture of the operator 11 of FIG. 2 and auto-selects a control mode for an associated work task 193 based on the detected gesture, doing so from the calibrated list of work tasks 93. This capability also allows the controller 50 to be programmed with a predetermined on/off gesture, such as a predetermined wave, rather than having the operator 11 physically activate a switch or an on/off button.

Optionally, the controller 50 may be programmed with a calibration mode. Such a mode may be desirable as each grasp assist device 10 may be worn at different times by different operators 11, and as each operator 11 may exhibit unique grasp characteristics relative to other operators 11. Thus, a one-size-fits-all design may be less than optimal. In such a calibration mode, the operator 11 of FIG. 2 may be prompted to move through a series or range of predetermined gestures and/or conduct predetermined work tasks while the controller 50 learns the operator's tendencies. In this manner, glove variance can be minimized between different operators 11.

Figure 4:
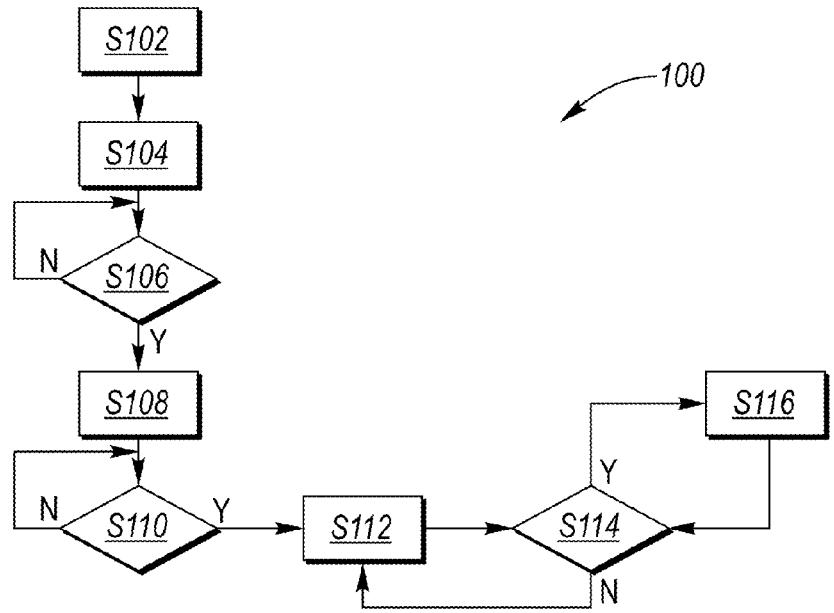
FIG. 4 is a flow chart describing an example method for controlling the grasp assist device shown in FIG. 1.

Referring to FIG. 4, an example embodiment of the method 100 for controlling the grasp assist device 10 of FIG. 1 begins with step S102 wherein the operator 11 puts on the grasp assist device 10 and then begins moving through the work space 60 as shown in FIG. 2. The method 100 then proceeds to step S104.

At step S104, the controller 50 next determines the location of the glove 12 within the work environment. For instance, the controller 50 may receive and process location signals (arrow $L_{10}$) from the location sensor 78 of FIG. 1, or may derive the location via the attitude sensors 88 as noted above and known in the art. This step enables the controller 50 to determine the location of the operator 11 wearing the glove 12 within the work environment 60. The method 100 then proceeds to step S106 as the location continues to be read and tracked by the controller 50.

Step S106 entails determining, again via the controller 50, whether the operator 11 has entered a predetermined work cell, e.g., $WC_A$, $WC_B$, or $WC_C$. For instance, the controller 50 may compare the present coordinates of the operator 11 to predetermined coordinates demarcating the perimeters of the various work cells $WC_A$, $WC_B$, and $WC_C$ to determine if the operator 11 has entered one of the work cells $WC_A$, $WC_B$, or $WC_C$. The method 100 proceeds to step S108 if the operator 11 has entered one of the work cells $WC_A$, $WC_B$, or $WC_C$. Otherwise, step S106 is repeated and the grasp assist device 10 remains off or in a default standby mode.

Step S108 entails identifying a work task from a list of permitted work tasks for the determined location of step S106 using the determined location and attitude. As part of step S108, the controller 50 extracts the calibrated list of work tasks 93, which is shown in FIG. 3 as the example work tasks $WT_1$, $WT_2$, $WT_3$, and $WT_4$. Completion of step S108 may include preventing the grasp assist device 10 from assisting in work tasks other than those of the calibrated list of work tasks 93. As such, the grasp assist device 10 is enabled at step S108 solely for a localized set of work tasks corresponding to the work to be performed in the present work cell. The controller 50 also reads the attitude signals (arrow $A_{10}$) from the attitude sensors 88 of FIG. 1 and proceeds to step S110.

As part of step S108 the controller 50 determines whether the received attitude signals (arrow $A_{10}$) correspond to one of the predetermined work tasks, permitted for the present work cell, e.g., work tasks $WT_1$, $WT_2$, $WT_3$, and $WT_4$ for example work cell $WC_A$. If so, the controller 50 extracts instructions from its memory (M) for assisting the detected task and proceeds to step S112. Otherwise, step S110 is repeated. Optionally, an alert or error message may be displayed via the display screen 42 of FIG. 1 if the operator's gestures do not match any of the authorized work tasks for the present work cell.

At step S112, the controller 50 receives measured actual grasping forces from the load sensors 28 of FIG. 1 as the force feedback signals (arrow 24) and calculates a required grasp assist force needed for assisting the operator 11 in performing of the identified work task. The controller 50 then commands application of the required grasp assist force to the glove 12 for the present authorized work task, such as by commanding application of a tensile force to the thumb portion 14 and a finger portion 15 of FIG. 1 via tendons 20 when manually tightening a lug nut, or assisting all finger portions 15 and the thumb portion 14 when lifting a heavy object. As this process continues the method 100 proceeds to step S114.

Step S114 includes detecting a default gesture of the operator 11 signaling a desire to temporarily disable the grasp assist device 10 of FIG. 1. By way of example, the controller 50 may be programmed with a default gesture such as a wave of the glove 12 back and forth in a set motion. The method 100 proceeds to step S116 when such a gesture is detected. Steps S112 and S114 otherwise continue in a loop until the operator 11 moves to another work task or departs the work cell, at which point the method 100 commences anew at step S102.

By using the above-described approach, those of ordinary skill in the art will appreciate that conventional operator-intensive grasp assistance controls may be optimized via the use of dynamic mode selection based on sensor data. Position information can be used to determine the location and heading of an operator, while inertial and joint angle/position sensors can provide attitude data, i.e., pitch, roll, yaw, etc. Together, the sensor data is processed with minimal operator interference to thereby increase operator efficiency.

Additionally, the number of possible control modes is increased relative to manually-selected/GUI-based devices, which are limited in large part due to the limited space on the sleeve 18 of FIG. 1 and the need for an operator to scroll through lists while wearing the grasp assist device 10, along with the requirement that the operator 11 will always make the appropriate mode selection from such displayed modes.

While the best modes for carrying out the disclosure have been described in detail, those familiar with the art to which this disclosure relates will recognize various alternative designs and embodiments for practicing the disclosure within the scope of the appended claims.

The invention claimed is:

1. A system comprising:
 a glove;
 a plurality of sensors positioned with respect to the glove, including load sensors configured to measure an actual grasping force applied to an object by an operator wearing the glove, and attitude sensors configured to determine an attitude of the glove;
 an actuator assembly operable for providing a grasp assist force via the glove; and
 a controller programmed with a respective location of each of a plurality of work cells in a work environment, and also with a set of permitted work tasks for each of the work cells, wherein the controller is further programmed to:
  determine a location of the glove within the work environment;
  determine the attitude of the glove within the detected location by processing the attitude signals from the attitude sensors;
  select a work task from a list of permitted work tasks for the detected location using the determined location and attitude;

calculate a required grasp assist force using the actual grasping force from the load sensors; and command an application of the required grasp assist force to the object, via the glove using the actuator assembly, to thereby assist the operator in performing the identified work task.

2. The system of claim 1, further comprising flexible tendons connected to the glove, wherein the actuator assembly is configured to apply the required grasp assist force by applying a tensile force to the flexible tendons.

3. The system of claim 1, wherein the plurality of sensors includes a location sensor configured to determine the location of the glove within the work environment.

4. The system of claim 3, wherein the location sensor is a global positioning system (GPS) sensor.

5. The system of claim 3, wherein the location sensor is a radio frequency identification (RFID) sensor.

6. The system of claim 1, wherein the attitude sensors include at least one accelerometer.

7. The system of claim 1, wherein the attitude sensors include at least one joint angle sensor.

8. The system of claim 1, further comprising a display screen in communication with the controller, wherein the controller is programmed to communicate information regarding the identified work task via the display screen.

9. The system of claim 1, wherein the controller is programmed to detect a predetermined gesture of the glove and to temporarily discontinue the commanded application of the required grasp assist force in response to the detected predetermined gesture.

10. A method for controlling a system having a glove, load sensors configured to measure an actual grasping force applied to an object by an operator wearing the glove, attitude sensors configured to determine an attitude of the glove, and an actuator assembly operable for applying a required grasp assist force to the glove, the method comprising:

determining a location of the glove within the work environment via a controller;

determining the attitude of the glove within the determined location, via the controller, by processing attitude signals from the attitude sensors;

identifying a work task from a list of permitted work tasks for the determined location using the determined location and attitude;

measuring, via the load sensors, an actual grasping force applied by the operator to an object;

calculating the required grasp assist force for the identified work task via the controller using the measured actual grasping force; and commanding an application of the required grasp assist force to the object, via the glove using the actuator assembly, to thereby assist the operator in performing the identified work task.

11. The method of claim 10, wherein the system includes flexible tendons connected to the glove, the method further comprising: applying the required grasp assist force by applying a tensile force to the flexible tendons.

12. The method of claim 10, wherein the system includes a location sensor operable for determining the location of the glove, and wherein determining the location of the glove includes processing a location signal from the location sensor using the controller.

13. The method of claim 12, wherein the location sensor is a global positioning system (GPS) sensor.

14. The method of claim 12, wherein the location sensor is a radio frequency identification (RFID) sensor.

15. The method of claim 10, wherein determining an attitude of the glove includes using an accelerometer as at least one of the attitude sensors.

16. The method of claim 10, wherein determining an attitude of the glove includes using a joint angle sensor as at least one of the attitude sensors.

17. The method of claim 10, further transmitting an output signal from the controller to a display screen within the determined location to thereby present information regarding the identified work task.

18. The method of claim 10, further comprising:

detecting a predetermined gesture of the glove; and temporarily discontinuing the application of the required grasp assist force in response to the detected predetermined gesture.

* * * * *